United States Patent [19]

Benardella

[11] Patent Number: Plant 7,166

[45] Date of Patent: Feb. 27, 1990

[54] MINIATURE ROSE PLANT NAMED BENJIM

[75] Inventor: Frank A. Benardella, Old Tappan, N.J.

[73] Assignee: Nor'East Miniature Roses, Inc., Rowley, Mass.

[21] Appl. No.: 245,000

[22] Filed: Sep. 15, 1988

[51] Int. Cl.[4] ..... A01H 5/00

[52] U.S. Cl. ..... Plt./7

[58] Field of Search ..... Plt. 7

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and unusual red and yellow bicolor miniature rose.

1 Drawing Sheet

SUMMARY OF THE INVENTION

The present invention relates to a new and distinct variety of rose plant of the miniature rose class, which was originated by my crossing as seed parent the variety known as "Rise'N Shine" (U.S. Plant Pat. No. 4,231) and as pollen parent the variety known as "Marina" (U.S. Plant Pat. No. 3,789). The varietal denomination of this new rose is "Benjim".

Among the novel characteristics possessed by this new variety which distinguishes it from its parents and all other varieties of which I am aware are its unusual red and yellow bicolored flowers in this class of rose. Flowers open well and retain bicolor effect as blooms age with red tones becoming pink and yellow coloring becoming near white. Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "16D" is plate 16D of The Royal Horticultural Society Colour Chart.

Parentage: Seedling.

*Seed parent.*—"Rise'N Shine".

*Pollen parent.*—"Marina".

Class: Miniature.

The following observations are made of specimens grown outdoors in Essex County, Mass., during the month of June.

FLOWER

Blooming habit: Recurrent.

A. Bud:

(1) *Size.*—Medium.

(2) *Form.*—Long pointed.

(3) *Color.*—As sepals divide, bud color is near 16D flushed with near 44A.

(4) *Sepals.*—Relatively smooth, longer than bud.

(5) *Penduncle.*—Length — about 1⅛ inch. Aspect — straight. Strength — erect. Color — near 144C.

B. Bloom:

(1) *Size.*—Average size when fully expanded — about 1⅝ inch.

(2) *Borne.*—Singly, one to a stem and in sprays of 3 to 5 blooms.

(3) *Form.*—High centered at first, becoming flat. Petals reflex and quill to points.

(4) *Petalage.*—Number of petals under normal conditions — about 18.

(5) *Color.*—After sepals fall and petals unfurl, predominant flower color viewing petals' top surface is near 45A, color of petal undersurface varies with outer petals showing distinct yellow coloring near 16D imbued with a red underlay producing an overall attractive contrast of red and yellow. General tonality at a distance. Color of petals at point of attachment is near 6B. As flowers age red coloring becomes magenta to pink and yellow coloring whitens.

C. Petals:

(1) *Texture.*—Medium.

(2) *Appearance.*—Inside velvety and outside satiny.

(3) *Form.*—Broad, fan shaped with pointed apices.

(4) *Arrangement.*—Regularly arranged, imbricated.

(5) *Petaloids in center.*—Few.

(6) *Persistence.*—Drop off cleanly.

(7) *Fragrance.*—Slightly spicy.

(8) *Lasting quality.*—Average lasting quality on plant and as cut flower.

REPRODUCTIVE ORGANS

A. Stamens, filaments and anthers:

Arrangement and color.—Regularly arranged around styles. Color — filaments near 16A.

B. Pollen:

*Color.*—Near 16B.

C. Styles: Medium length

D. Stigmas:
*Color.*—Near 4D.
E. Hips: None observed.

PLANT

A. Form: Compact, symmetrical.
B. Growth: Vigorous.
*Height attained.*—About 16 to 20 inches.
C. Foliage: Compound 5 to 7 leaflets.
(1) *Size.*—Medium.
(2) *Quantity.*—Abundant.
(3) *Color.*—New foliage: Upper side — near 148B. Under side — near 138B. Old foliage: Upper side — near 147A. Under side — near 138B.
(4) *Shape.*—Oval, pointed.
(5) *Texture.*—Upper side is semi-glossy; under side is matte.
(6) Edge.—Serrate.
(7) Serration.—Ordinary.
(8) Leaf stem.—Color — near 146A. Under side — 144A.
(9) *Stipules.*—Medium length, slightly bearded.

(10) *Resistance to disease.*—Blackspot — Good. Mildew — Good. Rust — Good.
D. Wood:
(1) New wood.—Color — near 146B. Bark — smooth.
(2) *Old wood.*—Color — near 146A. Bark — smooth.
E. Thorns:
(1) *Thorns.*—Quantity (main stalk) — average. On laterals from stalk — average. Form — long, thin, straight, curved downward. Length — medium. Color — near 199D. Position — irregular.
(2) *Prickles.*—None.
F. Winter hardiness: Needs protection in severe climates.

I claim:

1. A new and distinct variety of rose plant of the miniature rose class, and parts thereof, substantially as shown and described, characterized particularly by attractive red and yellow bicolored flowers.

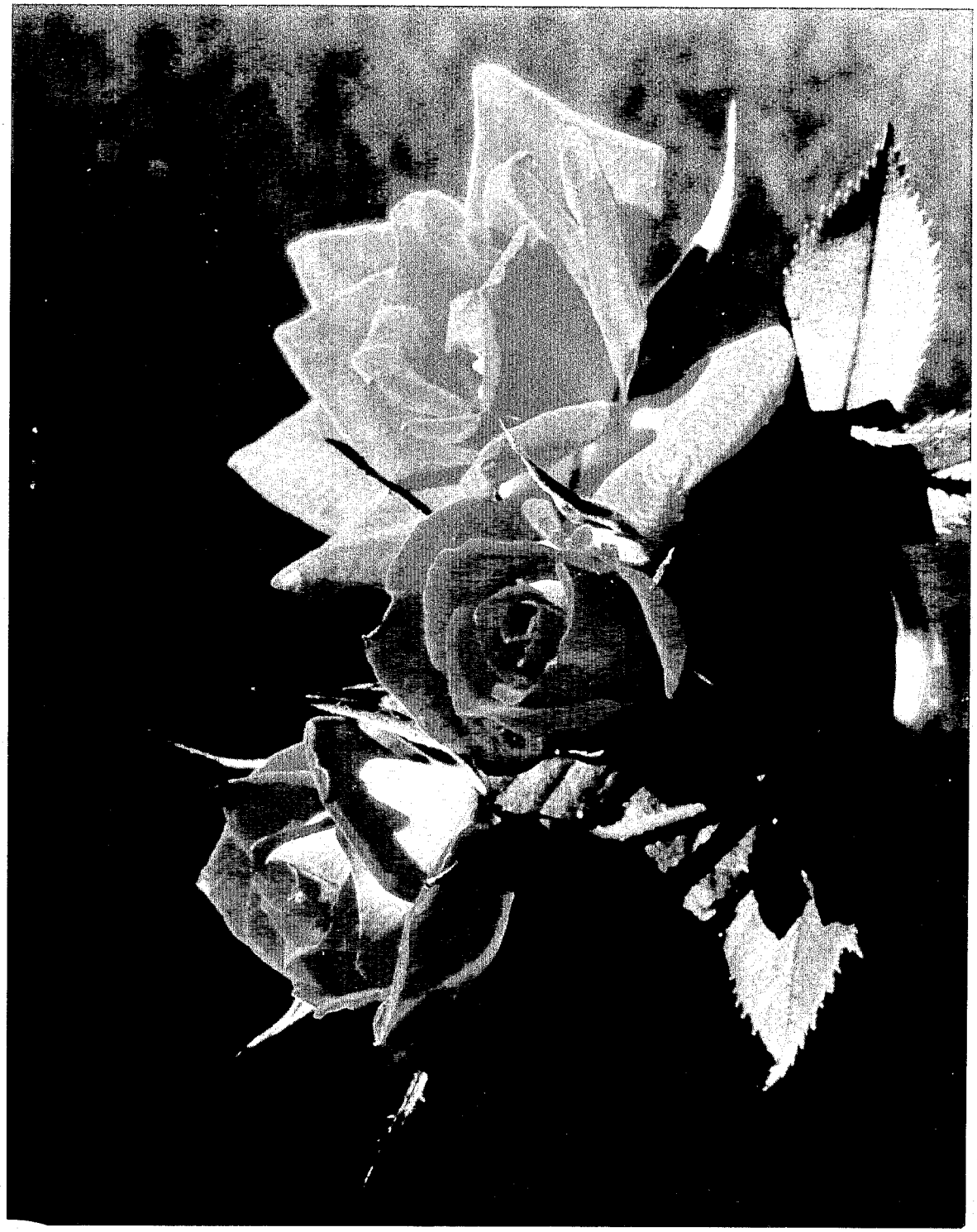

* * * * *